United States Patent
Hatada et al.

(10) Patent No.: US 11,464,216 B2
(45) Date of Patent: Oct. 11, 2022

(54) PRODUCTION METHOD FOR CONDITIONAL KNOCKOUT ANIMAL

(71) Applicant: NATIONAL UNIVERSITY CORPORATION GUNMA UNIVERSITY, Gunma (JP)

(72) Inventors: Izuho Hatada, Gunma (JP); Takuro Horii, Gunma (JP)

(73) Assignee: NATIONAL UNIVERSITY CORPORATION GUNMA UNIVERSITY, Gunma (JP)

(*) Notice: Subject to any disclaimer, the term of this patent is extended or adjusted under 35 U.S.C. 154(b) by 309 days.

(21) Appl. No.: 16/474,232

(22) PCT Filed: Dec. 27, 2017

(86) PCT No.: PCT/JP2017/046837
§ 371 (c)(1),
(2) Date: Jun. 27, 2019

(87) PCT Pub. No.: WO2018/124155
PCT Pub. Date: Jul. 5, 2018

(65) Prior Publication Data
US 2019/0357508 A1 Nov. 28, 2019

(30) Foreign Application Priority Data
Dec. 27, 2016 (JP) .............................. JP2016-254276

(51) Int. Cl.
*A01K 67/027* (2006.01)
*C12N 15/873* (2010.01)

(52) U.S. Cl.
CPC .... *A01K 67/0276* (2013.01); *A01K 2217/075* (2013.01); *A01K 2227/105* (2013.01)

(58) Field of Classification Search
None
See application file for complete search history.

(56) References Cited

U.S. PATENT DOCUMENTS

| | | | |
|---|---|---|---|
| 2014/0013457 A1 | 1/2014 | Murphy et al. | |
| 2016/0257974 A1* | 9/2016 | Bradley | C12N 15/102 |
| 2018/0064073 A1 | 3/2018 | Hashimoto et al. | |

FOREIGN PATENT DOCUMENTS

| | | | |
|---|---|---|---|
| JP | 2016-189796 | 11/2016 | |
| WO | WO-02088353 A2 * | 11/2002 | ............ C12N 15/63 |
| WO | 2016/133165 | 8/2016 | |

OTHER PUBLICATIONS

Brinster et al., Factors affecting the efficiency of introducing foreign DNA into mice by microinjecting eggs (PNAS, 1985, 82:4438-4442) (Year: 1985).*
International Preliminary Report on Patentability dated Aug. 24, 2018 in International Application No. PCT/JP2017/046837, with English translation.
International Search Report dated Mar. 27, 2018 in International Application No. PCT/JP2017/046837.
Horii, T. et al., "Efficient generation of conditional knockout mice via sequential introduction of lox sites", Scientific Reports, Aug. 11, 2017, vol. 7, No. 7891, pp. 1-8.
Nakagawa, Y. et al., "Ultra-superovulation for the CRISPR-Cas9-mediated production of gene-knockout, single-amino-acid-substituted, and floxed mice", Biology Open, Jul. 7, 2016, vol. 5, pp. 1142-1148, with supplementary information.
Menke, D.B., "Engineering Subtle Targeted Mutations Into the Mouse Genome", Genesis, 2013, vol. 51, pp. 605-618.
Nakao, H., et al., "A Possible Aid in Targeted Insertion of Large DNA Elements by CRISPR/Cas in Mouse Zygotes", Genesis, Jan. 17, 2016, vol. 54, pp. 65-77.
Lee, A., Yiu-Fai, et al., Conditional targeting of *Ispd* using paired Cas9 nickase and single DNA template in mice, FEBS Open Bio, 2014, vol. 4, pp. 637-642.
Yang, H., et al., "One-Step Generation of Mice Carrying Reporter and Conditional Alleles by CRISPR/Cas-Mediated Genome Engineering", Cell, 2013, vol. 154, No. 6, pp. 1370-1379.
Nakagawa, Y., et al., "Hyperlipidemia and hepatitis in liver-specific CREB3L3 knockout mice generated using a one-step CRISPR/Cas9 system", Scientific Reports, 2016, vol. 6, 27857, p. 1-11.

* cited by examiner

*Primary Examiner* — Arthur S Leonard
(74) *Attorney, Agent, or Firm* — Wenderoth, Lind & Ponack, L.L.P.

(57) ABSTRACT

A method of producing a conditional knockout animal, and techniques related thereto, e.g., a method of efficiently producing a floxed animal, are provided. By introducing recombinase recognition sequences such as loxP into both ends of a target region on a chromosome at different timings, an animal having the pair of recombinase recognition sequences on the chromosome, such as a floxed animal, is produced.

10 Claims, 2 Drawing Sheets

Specification includes a Sequence Listing.

PRODUCTION METHOD FOR CONDITIONAL KNOCKOUT ANIMAL

TECHNICAL FIELD

The present invention relates to a method of producing a conditional knockout animal, and techniques related thereto.

BACKGROUND ART

A function of a gene can be inferred by preparing an individual in which the gene is disrupted (knocked out), and then comparing its phenotype with that of a normal individual. Since mice have gene functions relatively similar to those of humans, and since they can be simply handled, a number of knockout mice have been prepared and used for gene function analysis. However, in a case where a gene functions in the whole body, and has an important role, simple knockout of the gene results in embryonic lethality (embryonic death resulting in prevention of the birth), so that gene function analysis with the individual is impossible. Conditional knockout is a method developed for solving this problem. In conditional knockout, a gene can be tissue-specifically or period-specifically knocked out, and therefore the embryonic lethality does not occur, so that gene function analysis is possible with born individuals.

As a method for preparing a conditional knockout mouse, for example, a Cre/loxP system or an Flp/FRT system is employed. In the Cre/loxP system, which is most frequently used, first, for example, sequences called loxP, each composed of 34 bases, are inserted in the intron portions (regions encoding no protein) at both ends of an exon (a region encoding a protein) of the gene to be knocked out such that the loxP sequences are arranged in the same direction. The state where the exon is sandwiched between the two loxP sequences is called flox (flanked loxP). In this stage, since the exon is not disrupted, the gene functions normally. In cases where the loxP sequences are arranged in the same direction, when Cre recombinase acts on the floxed chromosome, the region sandwiched between the loxP sequences is excised to be deleted. Thus, by crossing a floxed mouse with a mouse that tissue-specifically expresses Cre recombinase, a conditional knockout mouse having a gene knocked out only in the particular tissue can be obtained.

Preparation of a conditional knockout mouse has been conventionally carried out by a laborious operation in which a homologous recombinant ES cell having loxP introduced into a chromosome is established using an ES cell and a targeting cassette, and the cell is introduced into early embryos of mice to prepare chimeric mice, followed by crossing the mice to obtain offspring. With the rise of genome editing techniques such as CRISPR/Cas in recent years, direct modification of a chromosome of a fertilized egg has become possible. By this, for example, two loxP sequences can be introduced into a chromosome of a fertilized egg in one step to prepare a floxed mouse in a short time (Non-patent Documents 1 to 3).

PRIOR ART DOCUMENTS

Non-Patent Documents

Non-patent Document 1: Hui Yang, et al., One-step generation of mice carrying reporter and conditional alleles by CRISPR/Cas mediated genome engineering. Cell. 2013 Sep. 12; 154(6): 1370-1379.

Non-patent Document 2: Nakagawa Y, et al., Hyperlipidemia and hepatitis in liver-specific CREB3L3 knockout mice generated using a one-step CRISPR/Cas9 system. Sci Rep. 2016 Jun. 13; 6: 27857.

Non-patent Document 3: Yoshiko Nakagawa, et al., Ultra-superovulation for the CRISPR-Cas9-mediated production of gene-knockout, single-amino-acid-substituted, and floxed mice. Biology Open 2016 5: 1142-1148.

SUMMARY OF THE INVENTION

As described above, techniques in which two loxP sequences are introduced into a chromosome of a fertilized egg in one step to prepare a floxed mouse in a short time have been reported. However, the floxing efficiencies (the efficiencies with which floxed animals can be obtained) of these techniques are low.

An object of the present invention is to provide an efficient method of producing a conditional knockout animal, and techniques related thereto (a method of efficiently producing a floxed animal, and the like).

The present inventors intensively carried out a study to solve the above problem, and, as a result, inferred that the low floxing efficiencies of the above techniques may be due to the fact that deletion of the chromosome preferentially occurs because the chromosome is cleaved at two sites at the same time. The present inventors discovered that a high floxing efficiency can be achieved by introducing two loxP sequences at different timings (that is, in two separate steps) into the chromosome, thereby completing the present invention.

More specifically, the present invention can be exemplified as follows.

[1] A method of producing a transformed non-human animal, comprising:

(A) introducing a first recombinase recognition sequence into a chromosome of a non-human animal cell;

(B) introducing, after the Step (A), a second recombinase recognition sequence into the chromosome of the animal cell; and (C) obtaining, after the Step (B), a transformed non-human animal having the first and second recombinase recognition sequences introduced into the chromosome, from the animal cell;

wherein the first and second recombinase recognition sequences are base sequences between which recombination occurs by recombinase, and are introduced such that a target region on the chromosome is sandwiched between them.

[2] The method described above, wherein the first and second recombinase recognition sequences are loxP, VloxP, SloxP, rox, FRT, RS, or gix.

[3] The method described above, wherein the recombinase is Cre, VCre, SCre, Dre, FLP, R, or Gin.

[4] The method described above, wherein the introduction of the first and second recombinase recognition sequences is carried out by a CRISPR/Cas method, TALEN method, or ZFN method.

[5] The method described above, wherein the introduction of the first and second recombinase recognition sequences is carried out by electroporation.

[6] The method described above, wherein the introduction of the first and second recombinase recognition sequences is carried out by microinjection.

[7] The method described above, wherein the Steps (A) and (B) are carried out for a fertilized egg or an embryo.

[8] The method described above, wherein the Step (A) is carried out for a fertilized egg, and the Step (B) is carried out for a two-cell stage embryo.

[9] The method described above, wherein the transformed non-human animal is a monkey, chimpanzee, mouse, rat, hamster, guinea pig, rabbit, horse, cow, sheep, goat, pig, dog, or cat.

[10] The method described above, wherein the target region is a region containing an exon of a target gene.

[11] The method described above, wherein said method is a method of producing a conditional chromosome-modified non-human animal, and wherein the non-human animal cell is a non-human animal cell that conditionally expresses the recombinase, and the conditional chromosome-modified non-human animal is obtained by the Steps (A) to (C).

[12] A method of producing a conditional chromosome-modified non-human animal, comprising:
(X) obtaining the transformed non-human animal by the method described above; and
(Y) crossing the transformed non-human animal with a non-human animal that conditionally expresses the recombinase, to obtain a conditional chromosome-modified non-human animal.

[13] The method described above, wherein the non-human animal that conditionally expresses the recombinase is a non-human animal that tissue-specifically or period-specifically expresses the recombinase, or a non-human animal that expresses a recombinase that functions under particular conditions.

EMBODIMENTS FOR CARRYING OUT THE INVENTION

Figure 1:
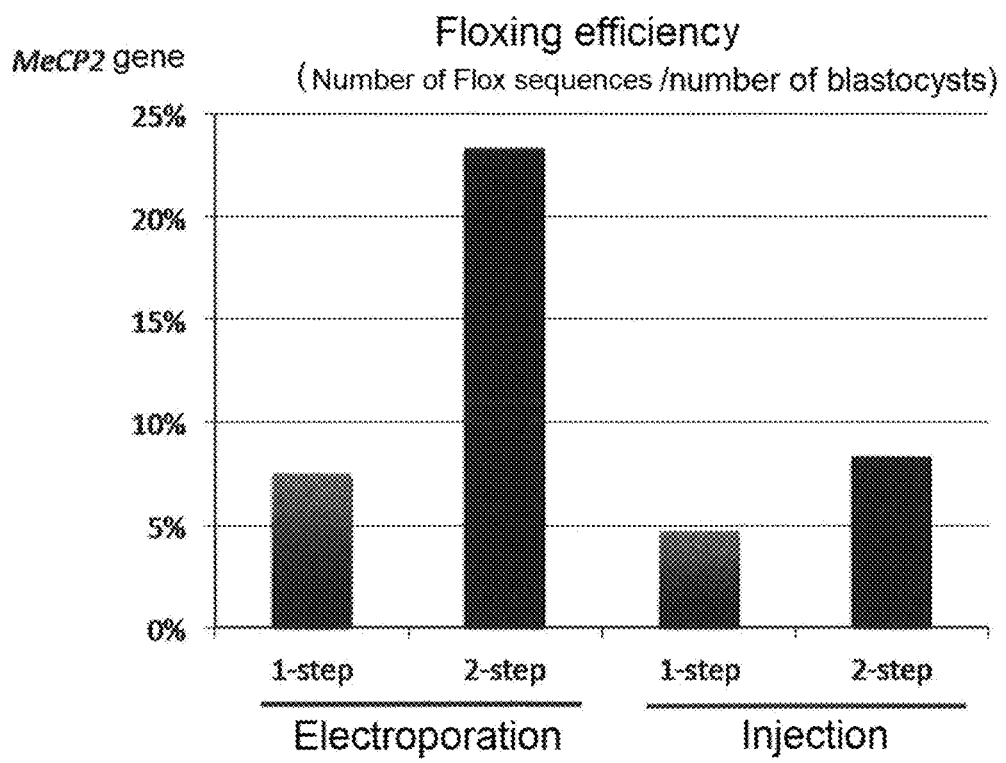
FIG. 1 is a diagram showing data on the floxing efficiency (Number of Flox sequences/number of blastocysts) for the MeCP2 gene in mouse blastocyst-stage embryos.

The present invention is described below in detail.
<1> Method of Producing Transformed Animal Cell and Transformed Animal The method of producing a transformed animal cell of the present invention is a method of producing a transformed animal cell, comprising a step of introducing first and second recombinase recognition sequences into a chromosome of an animal cell, wherein the introduction of the first and second recombinase recognition sequences is carried out at different timings (that is, in two separate steps). The transformed animal cell produced by this method is also referred to as "animal cell according to the present invention". In this method, the introduction of the first recombinase recognition sequence is carried out first, and the introduction of the second recombinase recognition sequence is then carried out. Hereinafter, the step of introducing the first recombinase recognition sequence is referred to as "Step (A)" or "Step A", and the step of introducing the second recombinase recognition sequence is referred to as "Step (B)" or "Step B".

In other words, the method of producing a transformed animal cell of the present invention is a method of producing a transformed animal cell, comprising the following Steps (A) and (B):
(A) introducing a first recombinase recognition sequence into a chromosome of an animal cell; and
(B) introducing, after the Step (A), a second recombinase recognition sequence into the chromosome of the animal cell.

From the transformed animal cell obtained, a transformed animal can be obtained. Thus, the method of producing a transformed animal of the present invention is a method of producing a transformed animal, comprising the steps of: producing a transformed animal cell by the above method; and obtaining a transformed animal from the transformed animal cell. The transformed animal produced by this method is also referred to as "transformed animal according to the present invention". The step of obtaining the transformed animal from the transformed animal cell is hereinafter referred to as "Step (C)" or "Step C".

In other words, the method of producing a transformed animal of the present invention is a method of producing a transformed animal, comprising the following Steps (A) to (C):
(A) introducing a first recombinase recognition sequence into a chromosome of an animal cell;
(B) introducing, after the Step (A), a second recombinase recognition sequence into the chromosome of the animal cell; and
(C) obtaining, after the Step (B), a transformed animal from the animal cell.

The animal cell according to the present invention and the animal according to the present invention are also collectively referred to as "transformant according to the present invention".

The type of the animal is not limited as long as it is an animal other than human (non-human animal). The non-human animal may be appropriately selected in accordance with conditions such as the use of the transformant according to the present invention. Examples of the non-human animal include non-human mammals, birds, reptiles, amphibians, fish, and insects. Examples of the non-human animal especially include non-human mammals. Examples of the non-human mammals include primates such as monkeys and chimpanzee; rodents such as mouse, rat, hamster, and guinea pig; and other non-human mammals such as rabbit, horse, cow, sheep, goat, pig, dog, and cat.

The "animal cell" means a cell of an animal. The type of the cell is not limited. The cell may be appropriately selected in accordance with conditions such as the use of the transformant according to the present invention. The cell may be either a single cell or multiple cells. Examples of the cell include fertilized eggs (undivided fertilized eggs), embryos, blastocysts, stem cells, somatic cells, and germ cells. Examples of the embryos include two-cell stage embryos and later-stage embryos.

The type of the cell for carrying out each step is not limited as long as the transformant according to the present invention can be obtained. For example, the type of the cell may change as the steps proceed. For example, after carrying out Step A, Step B may be carried out before cell division, or may be carried out after cell division. After carrying out Step A, Step B may be carried out especially after one or more times of cell division, or may be carried out more especially after one time of cell division. Examples of the cell to be subjected to Step A especially include fertilized eggs and embryos, more especially, fertilized eggs. Examples of the cell to be subjected to Step B especially include fertilized eggs and embryos, more especially, embryos. More specifically, for example, Step A may be carried out for a fertilized egg, and Step B may be carried out for an embryo. In particular, Step A may be carried out for a fertilized egg, and Step B may be carried out for a two-cell stage embryo. Examples of the cell to be subjected to Step C include cells capable of directly developing into an animal individual, especially fertilized eggs, embryos, and blastocysts.

The first and second recombinase recognition sequences are introduced such that the target region on the chromosome is sandwiched between them. Thus, the second modified chromosome has the first and second recombinase recognition sequences, and the region (target region) sandwiched between them. Similarly, the second transformed animal cell (animal cell according to the present invention) and the animal according to the present invention have the first and second recombinase recognition sequences, and the region (target region) sandwiched between these, on the chromosome.

The target region is the region to be modified by recombinase in the later-mentioned conditional chromosome-modified animal. The target region is not limited. The target region may be appropriately set in accordance with conditions such as the use of the transformant according to the present invention. Examples of the target region include regions containing a gene partially or entirely. Examples of the gene include a gene to be subjected to conditional knockout (target gene). Examples of the part of the gene include exons, introns, and expression regulatory sequences (for example, promoters). Examples of the part of the gene especially include exons. The target region may contain one gene partially or entirely, or may contain two or more genes partially or entirely. The target region may contain, for example, one region, or may contain two or more regions, selected from parts of these genes.

The first and second recombinase recognition sequences are introduced into both ends of the target region on the chromosome, respectively. More specifically, for example, by introducing the first and second recombinase recognition sequences into the introns at both ends of an exon, the first and second recombinase recognition sequences can be introduced such that the exon is sandwiched between them.

Into which end of the target region a recombinase recognition sequence is to be introduced first, that is, into which end of the target region the first recombinase recognition sequence is to be introduced, is not limited.

The first and second recombinase recognition sequences may be arranged in the same direction on the chromosome, or may be arranged in opposite directions on the chromosome.

The first and second recombinase recognition sequences are base sequences between which recombination occurs by recombinase. The first and second recombinase recognition sequences are not limited as long as the recombination occurs between them by recombinase. The recombinase (the recombinase that causes recombination between the first and second recombinase recognition sequences) is also referred to as "recombinase corresponding to the first and second recombinase recognition sequences". The term "occurrence of recombination between the first and second recombinase recognition sequences by recombinase" means that the first and second recombinase recognition sequences are recognized by the corresponding recombinase to cause modification of the region (target region) sandwiched between them. Examples of the modification of the target region include deletion or inversion of the target region. Examples of the modification of the target region especially include deletion of the target region. In general, when the first and second recombinase recognition sequences are arranged in the same direction on the chromosome, deletion of the target region may occur. In general, when the first and second recombinase recognition sequences are arranged in opposite directions on the chromosome, inversion of the target region may occur.

The combination of the recombinase recognition sequences and the recombinase that recognizes them is also referred to as "recombination system". Examples of the recombination system include the Cre/loxP system (B Sauer, Functional expression of the cre-lox site-specific recombination system in the yeast *Saccharomyces cerevisiae*. Mol. Cell. Biol.: 1987, 7(6); 2087-96.), the VCre/VloxP system (WO 2010/143606), the SCre/SloxP system (WO 2010/143606), the Dre/rox system (US 2006-094029 A1), the FLP/FRT system (J R Broach, et al., Recombination within the yeast plasmid 2mu circle is site-specific. Cell: 1982, 29(1); 227-34.), the R/RS system (H Araki, et al., Molecular and functional organization of yeast plasmid pSR1. J. Mol. Biol.: 1985, 182(2); 191-203.), and the Gin/gix system (S Maeser, R Kahmann, The Gin recombinase of phage Mu can catalyse site-specific recombination in plant protoplasts. Mol. Gen. Genet.: 1991, 230(1-2); 170-6.).

Thus, examples of the recombinase recognition sequence include loxP, VloxP, SloxP, rox, FRT, RS, and gix. Examples of the recombinase include Cre, VCre, SCre, Dre, FLP, R, and Gin, which correspond to loxP, VloxP, SloxP, rox, FRT, RS, and gix, respectively. The base sequences of these recombinase recognition sequences are shown in Table 1. The recombinase recognition sequences having the base sequences shown in Table 1 are also referred to as "wild-type recombinase recognition sequences". A recombinase recognition sequence is generally composed of inverted repeats at both ends, and a spacer region sandwiched between them. The spacer region defines the direction of the recombinase recognition sequence. For example, loxP is composed of 13-bp inverted repeats at both ends, and an 8-bp spacer region sandwiched between them. The term "the first and second recombinase recognition sequences are aligned in the same direction on the chromosome" means that the spacer regions of the recombinase recognition sequences are oriented in the same direction on the chromosome. The term "the first and second recombinase recognition sequences are aligned in opposite directions on the chromosome" means that the spacer regions of the recombinase recognition sequences are oriented in opposite directions on the chromosome.

TABLE 1

Table 1 Examples of wild-type recombinase recognition sequences

| Name | Base sequence (5' to 3') | SEQ ID NO: |
|---|---|---|
| loxP | ATAACTTCGTATA GCATACAT TATACGAAGTTAT | 13 |
| VloxP | TCAATTTCTGAGA ACTGTCAT TCTCGGAAATTGA | 14 |
| SloxP | CTCGTGTCCGATA ACTGTAAT TATCGGACATGAT | 15 |

TABLE 1-continued

Table 1 Examples of wild-type recombinase recognition sequences

| Name | Base sequence (5' to 3') | SEQ ID NO: |
|---|---|---|
| rox | TAACTTTAAATAAT GCCA ATTATTTAAAGTTA | 16 |
| FRT | GAAGTTCCTATTC TCTAGAAA GTATAGGAACTTC | 17 |
| RS | TTGATGAAAGAA TACGTTA TTCTTTCATCAA | 18 |
| gix | TTCCTGTAAACC GA GGTTTTGGATAA | 19 |

The recombinase recognition sequences may also be variants of the base sequences exemplified above as long as recombination occurs between the first and second recombinase recognition sequences by recombinase. The variants of the recombinase recognition sequences may be composed of base sequences having an identity of at least 50%, at least 60%, at least 70%, at least 75%, at least 80%, at least 85%, at least 90%, at least 95%, or at least 97%. The variants of the recombinase recognition sequences may also be composed of base sequences which are the same as the base sequences exemplified above except that, for example, one or several bases are substituted, deleted, inserted, and/or added. "One or several" may be, for example, 1 to 15, 1 to 12, 1 to 10, 1 to 8, 1 to 6, 1 to 5, 1 to 4, 1 to 3, 1 to 2, or 1. Examples of variants of loxP include lox66, lox71, lox511, lox2272, loxFAS, lox RE, and lox LE. Examples of variants of VloxP include Vlox2272, VloxM1, VloxM2, Vlox43R, and Vlox43L. Examples of variants of SloxP include Slox2272, SloxM1, SloxV1R, and SloxV1L. The base sequences of these variants are shown in Table 2.

TABLE 2

Table 2 Examples of variants of recombinase recognition sequences

| Name | Base sequence (5' to 3') | SEQ ID NO: |
|---|---|---|
| lox66 | TACCGTTCGTATA ATGTATGC TATACGAAGTTAT | 20 |
| lox71 | TACCGTTCGTATA GCATACAT TATACGAAGTTAT | 21 |
| lox511 | ATAACTTCGTATA GTATACAT TATACGAAGTTAT | 22 |
| lox2272 | ATAACTTCGTATA GGATACTT TATACGAAGTTAT | 23 |
| loxFAS | ATAACTTCGTATA TACCTTTC TATACGAAGTTAT | 24 |
| lox RE | ATAACTTCGTATA GCATACAT TATACGAACGGTA | 25 |
| lox LE | TACCGTTCGTATA GCATACAT TATACGAAGTTAT | 26 |
| Vlox2272 | TCAATTTCTGAGA AGTGTCTT TCTCGGAAATTGA | 27 |
| VloxM1 | TCAATTTCCGAGA ACTGTCAT TCTCGGAAATTGA | 28 |
| VloxM2 | TCAATTTCTGAGA ACTGTCAT TCTCAGAAATTGA | 29 |
| Vlox43R | TCAATTTCTGAGA ACTGTCAT TCTCGGAATACCT | 30 |
| Vlox43L | CGTGATTCTGAGA ACTGTCAT TCTCGGAAATTGA | 31 |
| Slox2272 | CTCGTGTCCGATA AGTGTATT TATCGGACATGAT | 32 |
| SloxM1 | CTCGTGTCCGATA ACTGTAAT TATCGGACACGAG | 33 |

TABLE 2-continued

Table 2 Examples of variants of recombinase recognition sequences

| Name | Base sequence (5' to 3') | SEQ ID NO: |
|---|---|---|
| SloxV1R | CTCGTGTCCGATA ACTGTAAT TATCGGACCGTCA | 34 |
| SloxV1L | TGACGGTCCGATA ACTGTAAT TATCGGACATGAT | 35 |

The recombinase recognition sequences specified by the names exemplified above are not limited to the wild-type recombinase recognition sequences exemplified above, and also include variants thereof. More specifically, for example, the term "loxP" includes not only the wild-type loxP (loxP of SEQ ID NO:13), but also variants of loxP such as lox66, lox71, lox511, lox2272, loxFAS, lox RE, and lox LE.

"Introducing a recombinase recognition sequence into a chromosome" is not limited to cases where a base sequence composed of the base sequence of a recombinase recognition sequence exemplified above is introduced into a chromosome, and also includes cases where a base sequence containing such a base sequence is introduced into a chromosome. Therefore, for example, "introducing a recombinase recognition sequence into a chromosome" also includes cases where a sequence in which a desired sequence such as a restriction enzyme recognition site or the like is added to the base sequence of a recombinase recognition sequence exemplified above is introduced into a chromosome.

The first and second recombinase recognition sequences may or may not be composed of the same base sequence as long as recombination occurs between them by recombinase. For example, a single base sequence selected from the group consisting of any wild-type recombinase recognition sequences and variants thereof may be commonly used as the first and second recombinase recognition sequences. More specifically, for example, a single base sequence selected from loxP (wild-type loxP and its variants) may be commonly used as the first and second recombinase recognition sequences. Alternatively, for example, two kinds of base sequences selected from the group consisting of any wild-type recombinase recognition sequences and variants thereof may be used as the first and second recombinase recognition sequences. More specifically, for example, two kinds of base sequences selected from loxP (wild-type loxP and its variants) may be used as the first and second recombinase recognition sequences. In both cases, the first and second recombinase recognition sequences are appropriately selected such that recombination occurs between them by recombinase. For example, although any loxP (wild-type loxP or its variant) is recognized by Cre, this does not mean that recombination by Cre occurs by any loxP combination. Thus, in cases where loxP is used as the first and second recombinase recognition sequences, a loxP combination that allows recombination by Cre is appropriately selected. In general, recombination by Cre occurs between recombinase recognition sequences composed of the same base sequence, for example, between wild-type loxP sequences or between lox2272 sequences. On the other hand, recombination by Cre does not occur between loxP and lox2272 (Experimental Medicine, November 2014, Vol. 32, No. 18). Specific examples of the combination of recombinase recognition sequences composed of different base sequences, which combination allows recombination by Cre, include the combination of lox66 and lox71.

Step A is a step of introducing a first recombinase recognition sequence into a chromosome of an animal cell.

Performing of Step A is referred to as, for example, "performing Step A for an animal cell" or "performing Step A for a chromosome".

By performing Step A, a chromosome into which the first recombinase recognition sequence is introduced (that is, a chromosome having the first recombinase recognition sequence) is produced. The chromosome (the chromosome produced by Step A) is also referred to as "first modified chromosome". More specifically, Step A may be a step of introducing a first recombinase recognition sequence into a chromosome of an animal cell to produce a first modified chromosome. By performing Step A, an animal cell in which the first recombinase recognition sequence is introduced into the chromosome (that is, an animal cell having the first recombinase recognition sequence on the chromosome), in other words, an animal cell having the first modified chromosome, is produced. The animal cell (the animal cell produced by Step A) is also referred to as "first transformed animal cell". Thus, Step A may be a step of introducing the first recombinase recognition sequence into the chromosome of the animal cell to produce the first transformed animal cell.

"First modified chromosome" is not limited to the chromosome itself in which the introduction of the first recombinase recognition sequence occurred in Step A, and also includes a chromosome produced from this chromosome through a process of replication or the like after the introduction as long as the resulting chromosome has the first recombinase recognition sequence. For example, in cases where the first transformed animal cell divides to produce a daughter cell having a daughter chromosome of the first modified chromosome, the daughter chromosome also corresponds to the "first modified chromosome". Similarly, "first transformed animal cell" is not limited to the animal cell itself in which the introduction of the first recombinase recognition sequence to the chromosome occurred in Step A, and also includes a cell produced from this animal cell through a process of cell division or the like after the introduction as long as the resulting cell has the first modified chromosome. For example, in cases where the first transformed animal cell divides to produce a daughter cell having a daughter chromosome of the first modified chromosome, the daughter cell also corresponds to the "first transformed animal cell".

Step B is a step of introducing a second recombinase recognition sequence into the chromosome after the Step A. More specifically, Step B is a step of introducing a second recombinase recognition sequence into the chromosome of the animal cell after the Step A. Step B is carried out after Step A. The term "the chromosome" as used for Step B means the chromosome as the subject of Step A for which Step A has already been carried out. Therefore, the term "the chromosome" as used for Step B means the chromosome into which the first recombinase recognition sequence is introduced by Step A, in other words, the first modified chromosome, more specifically, the first modified chromosome retained by the first transformed animal cell. The term "the animal cell" as used for Step B means the animal cell as the subject of Step A for which Step A has already been carried out. Therefore, the term "the animal cell" as used for Step B means the animal cell in which the first recombinase recognition sequence has been introduced into the chromosome by Step A, in other words, the first transformed animal cell. Thus, Step B means a step of introducing the second recombinase recognition sequence into the first modified chromosome, more specifically, a step of introducing the second recombinase recognition sequence into the first modified chromosome retained by the first transformed animal cell.

Performing of Step B is also referred to as, for example, "performing Step B for an animal cell (more specifically, the first transformed animal cell)" or "performing Step B for a chromosome (more specifically, the first modified chromosome)".

By performing Step B, the first modified chromosome into which the second recombinase recognition sequence is further introduced (that is, a chromosome having the first and second recombinase recognition sequences) is produced. The chromosome (the chromosome produced by Step B) is also referred to as "second modified chromosome". More specifically, Step B may be a step of introducing the second recombinase recognition sequence into the first modified chromosome to produce the second modified chromosome. By performing Step B, the animal cell in which the second recombinase recognition sequence is further introduced into the first modified chromosome (that is, an animal cell having the first and second recombinase recognition sequences on the chromosome), in other words, the animal cell having the second modified chromosome, is produced. The animal cell (the animal cell produced by Step B) is also referred to as "second transformed animal cell". The second transformed animal cell is, in other words, "animal cell according to the present invention". More specifically, Step B may be a step of introducing the second recombinase recognition sequence into the first modified chromosome, to produce the second transformed animal cell (animal cell according to the present invention).

"Second modified chromosome" is not limited to the chromosome itself in which the introduction of the second recombinase recognition sequence occurred in Step B, and also includes a chromosome produced from this chromosome through a process of replication or the like after the introduction as long as the resulting chromosome has the first and second recombinase recognition sequences. For example, in cases where the second transformed animal cell divides to produce a daughter cell having a daughter chromosome of the second modified chromosome, the daughter chromosome also corresponds to the "second modified chromosome". Similarly, "second transformed animal cell" is not limited to the animal cell itself in which the introduction of the second recombinase recognition sequence into the chromosome occurred in Step B, and also includes a cell produced from this animal cell through a process of cell division or the like after the introduction as long as the resulting cell has the second modified chromosome. For example, in cases where the second transformed animal cell divides to produce a daughter cell having a daughter chromosome of the second modified chromosome, the daughter cell also corresponds to the "second transformed animal cell".

Thus, by performing Step A and Step B, the animal cell according to the present invention can be obtained. The animal cell according to the present invention may be either heterozygous or homozygous regarding the second modified chromosome. In cases where the animal cell according to the present invention is constituted by a plurality of cells, the animal cells according to the present invention may be a mosaic regarding the second modified chromosome (more specifically, a mosaic of two or more kinds of cells selected from cells having the second modified chromosome as a heterozygote, cells having the second modified chromosome as a homozygote, and cells having no second modified chromosome).

Step C is a step of obtaining, after the Step B, a transformed animal from the animal cell. Step C is carried out after Step B. The term "the animal cell" as used for Step C means the animal cell as the subject of Steps A and B for which Steps A and B have already been carried out. Therefore, the term "the animal cell" as used for Step C means the animal cell in which the first and second recombinase recognition sequences have been introduced into the chromosome by Steps A and B, in other words, the second transformed animal cell. In other words, Step C is a step of obtaining a transformed animal from the second transformed animal cell.

Performing of Step C is also referred to as, for example, "performing Step C for an animal cell (more specifically, the second transformed animal cell)".

By performing Step C, an animal having the first and second recombinase recognition sequences on the chromosome, in other words, an animal having the second modified chromosome, can be obtained. The animal (the animal obtained by Step C) is, in other words, "animal according to the present invention". More specifically, Step C may be a step of obtaining the animal according to the present invention from the second transformed animal cell.

The "animal of the present invention" includes not only the animal individual which directly developed from the second transformed animal cell in Step C, but also an individual produced from this individual through a process of crossing, breeding, cloning, or the like as long as the individual has the second modified chromosome.

Thus, by performing Steps A to C, the animal according to the present invention can be obtained. The animal according to the present invention may be either heterozygous or homozygous regarding the second modified chromosome. In cases where the animal according to the present invention is heterozygous regarding the second modified chromosome, an animal individual which is homozygous regarding the second modified chromosome may be obtained as appropriate. For example, parents which are heterozygous regarding the second modified chromosome may be crossed with each other, and an individual which is homozygous regarding the second modified chromosome may be selected from the resulting offspring. Alternatively, in the animal according to the present invention, the second modified chromosome may be a mosaic. In cases where the animal according to the present invention is a mosaic regarding the second modified chromosome, an animal individual which is not a mosaic regarding the second modified chromosome (more specifically, an animal individual which is heterozygous or homozygous regarding the second modified chromosome) may be obtained as appropriate. For example, a parent which is a mosaic regarding the second modified chromosome may be crossed with a wild-type parent of the same species, and an individual which is heterozygous regarding the second modified chromosome may be selected from the resulting offspring.

Retaining of the second modified chromosome by the transformant according to the present invention can be confirmed by, for example, a known method for determining the chromosomal structure. Examples of such a method include base sequence analysis of the region in which the first and second recombinase recognition sequences are introduced, and determination of the size of a PCR amplification fragment of the region in which the first and second recombinase recognition sequences are introduced. More specifically, retaining of the second modified chromosome by the transformant according to the present invention can be confirmed by, for example, the method described in Example.

Means for introducing the recombinase recognition sequences into the chromosome is not limited as long as the recombinase recognition sequences can be introduced into predetermined sites in the chromosome. The introduction of the recombinase recognition sequences can be carried out by, for example, a known site-specific genome editing. Examples of the site-specific genome editing include methods using nucleases. Specific examples of such methods include the CRISPR/Cas (CRISPR: clustered regularly interspaced short palindromic repeat, Cas: CRISPR-associated protein) method, the TALEN (transcription-activator like effector nuclease) method, and the ZFN (Zinc finger nuclease) method. These methods use Cas, TALEN, and ZFN, respectively, as nucleases.

The CRISPR/Cas method can be carried out using, for example, Cas, guide RNA (gRNA), and donor DNA. Examples of the Cas include Cas9 and Cpf1. The CRISPR/Cas method using Cas9 as the Cas is also called "CRISPR/Cas9 method", and the CRISPR/Cas method using Cpf1 as the Cas is also called "CRISPR/Cpf1 method". The guide RNA may be appropriately designed such that the recombinase recognition sequences can be introduced into predetermined sites in the chromosome. Instead of the guide RNA, a combination of crRNA and tracrRNA may be used. In cases of Cpf1, crRNA may be used alone as the guide RNA.

The TALEN method can be carried out using TALEN and donor DNA. TALEN has a TAL effector as a module that recognizes a particular base sequence. The TAL effector may be appropriately designed such that the recombinase recognition sequences can be introduced into predetermined sites in the chromosome.

The ZFN method can be carried out, for example, using ZFN and donor DNA. ZFN has a zinc finger domain as a module that recognizes a particular base sequence. The zinc finger domain may be appropriately designed such that the recombinase recognition sequences can be introduced into predetermined sites in the chromosome.

The nuclease may be either a wild-type nuclease or a variant thereof. The variant is not limited as long as the recombinase recognition sequences can be introduced into predetermined sites in the chromosome. Examples of variants of Cas9 include Cas9 (D10A) and Cas9 (H840A), which function as nickase. In cases where nickase is used in the CRISPR/Cas method, two kinds of guide RNA may be used in combination. Examples of variants of TALEN include Platinum TALEN (Sakuma T, et. al., (2013) Repeating pattern of non-RVD variations in DNA-binding modules enhances TALEN activity. Sci Rep 3: 3379.) and GoldyTALEN (Bedell V M, et al., In vivo genome editing using a high-efficiency TALEN system. Nature. 2012 Nov. 1; 491(7422): 114-8.).

The donor DNA is DNA containing a recombinase recognition sequence. In the above methods, the recombinase recognition sequence can be incorporated into the chromosome by homologous recombination repair utilizing the donor DNA. The donor DNA may be selected taking into account conditions such as the type of the method selected. The donor DNA may be, for example, either linear or circular. The donor DNA may be, for example, either a single strand or a double strand. More specifically, the donor DNA may be, for example, single-stranded linear DNA.

The introduction of the recombinase recognition sequence can be carried out, more specifically, by introducing a required substance(s) suitable for the method selected, into the cell. Examples of the required substance(s) in a case of the CRISPR/Cas method include nuclease; RNA such as gRNA; and donor DNA. Examples of the required substance(s) in a case of the TALEN method or the ZFN method include nuclease and donor DNA.

The nuclease may be, for example, directly introduced into the cell, or may be indirectly introduced into the cell by allowing its expression in the cell. For example, mRNA encoding the nuclease or a vector encoding the nuclease may be introduced into the cell, and the nuclease may be expressed from the mRNA or the vector. Similarly, the RNA such as gRNA may be, for example, directly introduced into the cell, or may be indirectly introduced into the cell by allowing its expression in the cell. For example, a vector encoding RNA such as gRNA may be introduced into the cell, and the RNA such as gRNA may be expressed from the vector. Similarly, the donor DNA may be, for example, directly introduced into the cell. The DNA used may be either a single strand or a double strand. A PCR fragment, a synthetic oligonucleotide, and/or a vector may be used. Examples of the vector include plasmid vectors and virus vectors. In cases where two or more kinds of required substances are expressed from a vector(s), the required substances may be encoded together in a single vector, or may be encoded separately in a plurality of vectors. The vector(s) may serve as the donor DNA at the same time.

As the required substance(s), or the mRNA or the vector(s) encoding the required substance(s) (hereinafter also collectively referred to as "required substance(s) or the like"), a commercially available product(s) may be used when available, or a product(s) prepared as appropriate may be used. The nuclease may be produced using, for example, a heterologous protein expression system or a cell-free protein expression system. The RNA such as mRNA or gRNA may be produced by, for example, chemical synthesis or in vitro transcription. The donor DNA may be produced by, for example, chemical synthesis or PCR amplification. The vector encoding RNA such as nuclease or gRNA may be produced by, for example, chemical synthesis or cloning.

Means for introducing the required substance(s) or the like into the cell is not limited. The introduction of the required substance(s) may be carried out by, for example, a known method for introduction of a component such as protein or nucleic acid into the cell. Specific examples of such a method include electroporation, microinjection, and lipofection. In cases of a virus vector, the vector may be introduced into the cell by infection of the cell with the vector. Examples of such a method especially include electroporation and microinjection. Examples of such a method more especially include electroporation. In particular, it is expected that use of electroporation can improve the success rate of the method of the present invention compared to cases where other methods such as microinjection are used. Examples of the improvement of the success rate of the method of the present invention include improvement of the cell survival rate, and improvement of the efficiency of introduction of the first and second recombinase recognition sequences.

Means for obtaining the animal of the present invention from the second transformed animal cell (animal cell of the present invention) is not limited. More specifically, the term "obtaining the animal from the cell" means allowing the animal individual to develop from the cell. The development of the animal individual from the cell can be carried out by, for example, a known method. For example, in cases where the cell is a cell that can directly develop into an animal individual such as a fertilized egg, embryo, blastocyst, or the like, the individual can be directly allowed to develop from the cell. More specifically, for example, by transplanting the cell to a pseudopregnant mother and allowing development and delivery, the animal individual can be obtained as an offspring. Alternatively, for example, the animal individual can be allowed to develop by cloning from a cell such as a stem cell or a somatic cell.

<2> Method of Production of Conditional Chromosome-Modified Animal

By crossing the transformed animal according to the present invention with a conditional recombinase-expressing animal, a conditional chromosome-modified animal can be obtained. More specifically, the method of producing a conditional chromosome-modified animal of the present invention is a method of producing a conditional chromosome-modified animal, comprising: producing a transformed animal according to the present invention by the above method; and crossing the resulting transformed animal with a conditional recombinase-expressing animal. The conditional chromosome-modified animal produced by this method is also referred to as "conditional chromosome-modified animal according to the present invention".

In other words, the method of producing a conditional chromosome-modified animal of the present invention is a method of producing a conditional chromosome-modified non-human animal, comprising the following Steps (X) and (Y):

(X) performing the above Steps (A) to (C) to obtain a transformed non-human animal from the animal cell; and (Y) crossing the transformed animal with a conditional recombinase-expressing animal, to obtain a conditional chromosome-modified non-human animal.

Step (Y) is a step of crossing the animal according to the present invention with a conditional recombinase-expressing animal.

Performing of Step (Y) is also referred to as, for example, "performing Step (Y) for the animal (more specifically, the animal according to the present invention)".

The term "conditional recombinase-expressing animal" means an animal that conditionally expresses a recombinase corresponding to the first and second recombinase recognition sequences. The recombinases corresponding to the respective recombinase recognition sequences are as described above.

The recombinase may be either a wild-type recombinase or a variant thereof. The variant is not limited as long as recombination occurs between the first and second recombinase recognition sequences. Examples of variants of Cre include Cre-ER.

Examples of the conditional recombinase-expressing animal include animals that tissue-specifically or period-specifically express recombinase. The tissue-specific or period-specific expression of recombinase can be achieved by, for example, allowing expression of the recombinase under regulation by a tissue-specific promoter or a period-specific promoter. Thus, examples of the animals that tissue-specifically or period-specifically express recombinase include animals having a recombinase gene whose expression occurs under regulation by a tissue-specific promoter or a period-specific promoter.

Examples of the conditional recombinase-expressing animal also include animals that express a recombinase which functions under particular conditions. Examples of the recombinase that functions under particular conditions include Cre-ER, which is a variant of Cre. Cre-ER is a fusion protein between Cre and a mutant estrogen receptor, and normally present in cytoplasm. When the protein is bound to an estrogen derivative tamoxifen, it is transferred into the nucleus, and causes loxP recombination. Thus, Cre-ER is a recombinase that functions in the presence of tamoxifen.

As the conditional recombinase-expressing animal, a commercially available product may be used when available, or a product prepared as appropriate may be used. The conditional recombinase-expressing animal may be produced by, for example, knock-in of a recombinase gene to the initiation codon site of a gene that is tissue-specifically or period-specifically expressed, or knock-in of a recombinase gene linked downstream of a tissue-specific promoter or a period-specific promoter. The knock-in of the gene may be carried out by a conventional method. The conditional recombinase-expressing animal may be produced by, for example, performing knock-in of a recombinase that functions under particular conditions, in a manner enabling its expression. Alternatively, a transgenic animal with a construct in which a recombinase gene is linked downstream of a tissue-specific or period-specific transcriptional regulatory sequence, or a transgenic animal with a recombinase construct that functions under particular conditions may be used.

When Step (Y) is carried out, the recombinase functions under, for example, drug-induced, tissue-specific, or period-specific conditions, resulting in modification of the target region on the chromosome. More specifically, by performing Step (Y), an animal in which the target region on the chromosome can be conditionally modified, or in which the target region on the chromosome has been conditionally modified, can be obtained. The animal (the animal obtained by Step (Y)) is, in other words, "conditional chromosome-modified animal according to the present invention". More specifically, Step (Y) may also be a step of crossing the animal according to the present invention with a conditional recombinase-expressing animal, to obtain the conditional chromosome-modified animal according to the present invention.

Examples of the modification of the target region include deletion or inversion of the target region. By the modification of the target region, the gene can be, for example, disrupted (knocked out). More specifically, for example, in cases where the target region contains a gene partially or entirely, the gene can be disrupted by the modification of the target region. Thus, examples of the conditional chromosome-modified animal include conditional gene-disrupted animals (conditional gene-knockout animals).

Examples of "conditional chromosome-modified animal according to the present invention" includes not only an animal individual itself directly born by crossing of the animal according to the present invention with the conditional recombinase-expressing animal in Step (Y), but also an individual produced through a process such as crossing, breeding, cloning, or the like from this individual, as long as the individual is modified such that the recombinase conditionally functions (more specifically, the target region on the chromosome can be conditionally modified, or the target region on the chromosome has been conditionally modified).

Thus, by performing Steps (A) to (C) and (Y), the conditional chromosome-modified animal according to the present invention can be obtained.

Alternatively, by performing Steps (A) to (C) for a cell of the conditional recombinase-expressing animal, the conditional chromosome-modified animal according to the present invention can be obtained without performing Step (Y).

Thus, in one mode, the animal according to the present invention may have the same meaning as the conditional chromosome-modified animal according to the present invention. One mode of the method of producing a transformed animal cell according to the present invention may be a method of producing a conditional chromosome-modified animal wherein the animal cell (the animal cell to be subjected to Steps (A) to (C)) is a cell of a conditional recombinase-expressing animal, and wherein a conditional chromosome-modified animal is obtained by Step (A) to (C).

Further, from the conditional chromosome-modified animal of the present invention, a conditional chromosome-modified animal cell can also be obtained.

The conditional chromosome-modified animal of the present invention and the cell thereof (conditional chromosome-modified animal cell) can be used for, for example, functional analysis of a target region (for example, a gene) on a chromosome.

EXAMPLES

The present invention is described below more concretely by way of an Example. However, the present invention is not limited thereby.

Example: Preparation of Floxed Mice by Two-Step Introduction

<1> Materials and Methods

<1-1> Providing of Fertilized Eggs

Fertilized eggs were provided basically according to Horii et al., Sci Rep. 4: 4513, 2014. More specifically, 7.5 U of pregnant mare serum gonadotropin (PMSG) was intraperitoneally administered to each female BDF1 mouse of 8 to 10 weeks old (CLEA Japan, Inc.), and 7.5 U of human chorionic gonadotropin (hCG) was intraperitoneally administered thereto 48 hours thereafter, followed by crossing the mouse with a male mouse of the same strain. On the next day, whether mating occurred successfully was checked by observing the presence or absence of a vaginal plug. In the afternoon of the same day, female mice whose successful mating could be confirmed were euthanized, and oviducts were recovered therefrom, followed by collecting fertilized eggs from the oviducts into M2 hyaluronidase liquid. After confirming separation of cumulus cells, the fertilized eggs were transferred to M16 medium, and cultured in a $CO_2$ incubator (5% $CO_2$, 37° C.) until operation.

<1-2> Cas9, gRNA, and ssODN

As Cas9, a commercially available recombinant protein (Thermo Fisher Scientific Inc.) was used.

As gRNA, RNAs having the base sequences shown in Table 3 (wherein T should be read as U) were synthesized for the MeCP2 gene and for the Tet3 gene. In the table, each underline indicates a chromosome binding region. The synthesis of the gRNA was carried out according to a method using a synthetic oligo DNA as a template or a method using, as a template, DNA amplified from a gRNA vector by PCR (Horii et al., Int J Mol Sci. 14:19774-81, 2013). More specifically, in vitro transcription was carried out using a MEGAshortscript T7 Kit (Thermo Fisher Scientific Inc.), followed by purification using a MEGAclear Kit (Thermo Fisher Scientific Inc.).

[Table 3]

TABLE 3 gRNA

< gRNA for MeCP2 gene >

| | Name | Base sequence (5' to 3') | SEQ ID NO: |
|---|---|---|---|
| gRNA1 | MeCP2-L2 | gCCCAAGGATACAGTATCCTAGTTTTAGAGCTAGAAATAG<br>CAAGTTAAAATAAGGCTAGTCCGTTATCAACTTGAAAAAG<br>TGGCACCGAGTCGGTGCTTTT | 1 |
| gRNA2 | MeCP2-R1 | gAGGAGTGAGGTCTAGTACTTGTTTTAGAGCTAGAAATAG<br>CAAGTTAAAATAAGGCTAGTCCGTTATCAACTTGAAAAAG<br>TGGCACCGAGTCGGTGCTTTT | 2 |

< gRNA for Tet3 gene >

| | Name | Base sequence (5' to 3') | SEQ ID NO: |
|---|---|---|---|
| gRNA1 | Tet3Ex8-2 | ggTTCCCAGCAATGGTTCTGGGTTTTAGAGCTAGAAATAG<br>CAAGTTAAAATAAGGCTAGTCCGTTATCAACTTGAAAAAG<br>TGGCACCGAGTCGGTGCTTTT | 3 |
| gRNA2 | Tet3Ex9-3 | ggTCTAAGCCAACACTACCTAGTTTTAGAGCTAGAAATAG<br>CAAGTTAAAATAAGGCTAGTCCGTTATCAACTTGAAAAAG<br>TGGCACCGAGTCGGTGCTTTT | 4 |

As ssODNs (single-stranded oligodeoxynucleotides) to be used as donor DNAs, DNAs having the base sequences containing loxP shown in Table 4 were synthesized for the MeCP2 gene and for the Tet3 gene. In the table, the upper-case letters indicate loxP sequences, and the bold underlines indicate exogenous restriction sites. MeCP2-L2-lox66 and MeCP2-R1-lox71, which are for the MeCP2 gene, include lox66 and lox71, respectively. Tet3Ex8-2loxPL and Tet3Ex9-3loxPR, which are for the Tet3 gene, include loxP in common.

Cas9/gRNA/ssODN solutions (solutions containing Cas9, gRNA, and ssODN) were prepared as follows immediately before the introduction, and the resulting concentrations were used as standard concentrations. Each concentration represents the final concentration. For injection, dilution was performed with RNase-free water. For electroporation, dilution was performed with Opti-MEM (Thermo Fisher Scientific).

TABLE 4 ssODN

< ssODN for MeCP2 gene >

| | Name | Base sequence (5' to 3') | SEQ ID NO: |
|---|---|---|---|
| ssODN1 | MeCP2-L2-lox66 | ccagcaacctaaagctgttaagaaatctttgggccccagc<br>ttgacccaaggatacagtatgctagcTACCGTTCGTATAA<br>TGTATGCTATACGAAGTTATcctagggaagttaccaaaat<br>cagagatagtatgcagcagccaggggtctcatgtgtggca | 5 |
| ssODN2 | MeCP2-R2-lox71 | ccactcctctgtactccctggcttttccacaatccttaaa<br>ctgaaggagtgaggtctagtTACCGTTCGTATAGCATACA<br>TTATACGAAGTTATgaattcacttgggggtcattgggcta<br>gactgaatatctttggttggtacccagacctaatccacca | 6 |

< ssODN for Tet3 gene >

| | Name | Base sequence (5' to 3') | SEQ ID NO: |
|---|---|---|---|
| ssODN1 | Tet3Ex8-2loxPL | accaggggaacgctgagaccctggacgcacttggcttcct<br>gtcttcccagcaatggttctggatccATAACTTCGTATAG<br>CATACATTATACGAAGTTATggtgggctcatttctggcag<br>gaagtttgccggcttgagcagctctgaatgtacctattg | 7 |
| ssODN2 | Tet3Ex9-3loxPR | actgatctgagggttatctctgtggaagggcaggagcagg<br>ccatctaagccaacactaccATAACTTCGTATAATGTATG<br>CTATACGAAGTTATgaattctagggcttcaagaatccact<br>ctacttccctcctcacaagtagcaaaacccattagttggc | 8 |

<Composition of Solution for One-Step>

| Cas9 nuclease | 100 ng/µL |
|---|---|
| gRNA1 | 24 ng/µL |
| gRNA2 | 24 ng/µL |
| ssODN1 | 400 ng/µL |
| ssODN2 | 400 ng/µL |

<Composition of Solution for Two-Step>
<First Step>

| Cas9 nuclease | 100 ng/µL |
|---|---|
| gRNA1 | 24 ng/µL |
| ssODN1 | 400 ng/µL |

<Second Step>

| Cas9 nuclease | 100 ng/µL |
|---|---|
| gRNA2 | 24 ng/µL |
| ssODN2 | 400 ng/µL |

<1-3> Microinjection

Fertilized eggs 24 to 27 hours after the hCG injection were subjected to injection. The Cas9/gRNA/ssODN solution was injected into the pronucleus using a micromanipulator under an inverted microscope. When two-step injection was carried out, the second injection was performed 42 to 44 hours after the hCG (at the two-cell stage). In a preliminary experiment, the stock solution, a 1:2 dilution, or a 1:4 dilution of the Cas9/gRNA/ssODN solution was injected in one step, and the rate of development to the blastocyst was investigated. As a result, the stock solution caused developmental arrest in most embryos. Thus, in this experiment, a 1:2-dilution of the Cas9/gRNA/ssODN solution was used for both of the one-step and two-step cases.

<1-4> Electroporation

Fertilized eggs 24 to 27 hours after the hCG injection were subjected to electroporation. When two-step electroporation was carried out, the second electroporation was performed 42 to 44 hours after the hCG (at the two-cell stage). In this experiment, the stock solution of the Cas9/gRNA/ssODN solution was used for both of the one-step and two-step cases. As an electroporator, CUY21 EDIT (BEX Co., Ltd.) was used, and, unless otherwise specified, electroporation was carried out under the conditions of: 30 V (3 msec ON+97 msec OFF)×seven pulses. Tetraploid embryos produced as a result of electrofusion were removed about 30 minutes later, and only diploid embryos were used for the subsequent experiments.

<1-5> In Vitro Culture and Embryo Transfer

Part of the treated embryos obtained in <1-3> and <1-4> were subjected to in vitro culture until the blastocyst stage, and the rate of development and the genotype were assayed. Other treated embryos were transferred at the two-cell stage into oviducts of pseudopregnant mice. About 20 days after the transfer, offspring were obtained.

<1-6> Genotype Assay

From the blastocyst or the tail of each offspring, DNA was extracted. Using the DNA as a template, a region containing two loxP sequences was amplified by PCR. The primer set used is shown in Table 5.

TABLE 5

Primers for genotype assay

| Name | Base sequence (5' to 3') | SEQ ID NO: |
|---|---|---|
| <Primers for MeCP2-flox assay> | | |
| Mecp2loxPCheck-1 | AAGAAGCCAACCATACAGTGC | 9 |
| Mecp2loxPCheck-2 | GCTTGCTCAGAAGCCAAAAC | 10 |
| <Primers for Tet3-flox assay> | | |
| Tet3Ex8&9-1 | GAACGCTGAGACCCTGGAC | 11 |
| Tet3Ex8&9-2 | ATTCACACGTTGGCTCTGGT | 12 |

Annealing at 60° C., Wild type 983 bp, floxed 1,063 bp
Annealing at 60° C., Wild type 995 bp, floxed 1,108 bp In cases where the ssODN was inserted, the restriction sites inserted together with loxP (NheI and EcoRI in the case of MeCP2, or BamHI and EcoRI in the case of Tet3) can be cleaved by restriction enzyme treatment. Thus, after the restriction enzyme treatment of the PCR product, agarose gel electrophoresis was carried out, and the presence or absence of insertion of the ssODN was investigated based on the length of the band. For part of the samples for the MeCP2 gene and all samples for the Tet3 gene, TA-cloning was carried out using the PCR product to investigate the base sequence.

<2> Results

Figure 2:
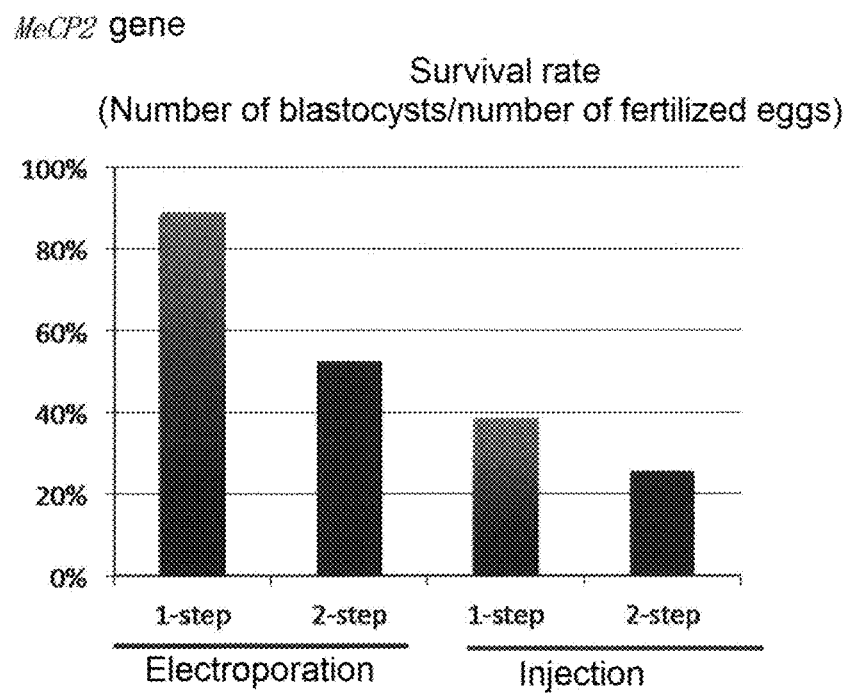
FIG. 2 is a diagram showing data on the survival rate (number of blastocysts/number of fertilized eggs) for the MeCP2 gene in mouse blastocyst-stage embryos.
Figure 3:
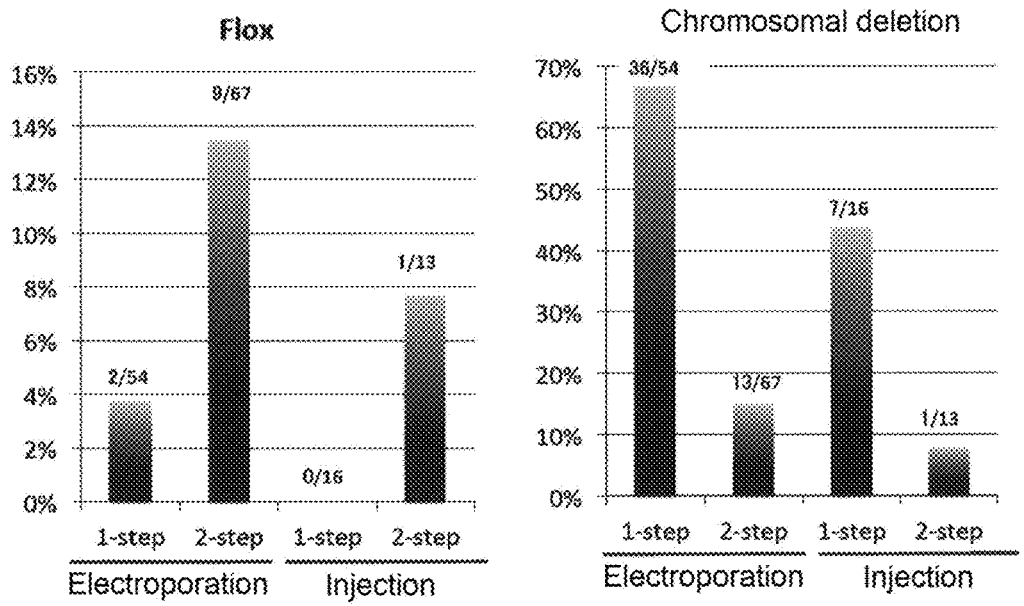
FIG. 3 is a diagram showing data on the floxing efficiency and the rate of chromosomal deletion for the MeCP2 gene in mouse offspring.

FIG. 1 is a diagram showing data on the floxing efficiency (Number of Flox sequences/number of blastocysts) for the cases of the MeCP2 gene in the blastocyst-stage embryos. FIG. 2 is a diagram showing data on the survival rate (number of blastocysts/number of fertilized eggs) for the cases of the MeCP2 gene in the blastocyst-stage embryos. FIG. 3 is a diagram showing data on the floxing efficiency and the rate of chromosomal deletion for the cases of the MeCP2 gene in the offspring.

As shown in FIG. 1, either the microinjection or the electroporation resulted in a better floxing efficiency in the case where the two loxP sequences were introduced in two separate steps, compared to the case where the two loxP sequences were introduced in one step. In particular, the highest floxing efficiency could be obtained in the case of two-step electroporation. More specifically, the conventional method (one-step microinjection) resulted in a floxing efficiency of slightly less than 5%, while the two-step electroporation resulted in a floxing efficiency of 23%, which is a 4.6 times higher efficiency.

Further, as shown in FIG. 2, in either the microinjection or the electroporation, the introduction of the two loxP sequences in two separate steps resulted in a lower survival rate compared to that in the case where the two loxP sequences were introduced in one step. However, the electroporation showed better survival rates compared to the microinjection. The improvement of the survival rate by the electroporation is thought to be due to the fact that electroporation causes less physical damage to embryos compared to microinjection. In particular, the survival rate in the case of the two-step electroporation was found to be 1.4 times higher than that in the case of the conventional method (one-step microinjection).

Thus, in the case of the two-step electroporation, 6.4 times (4.6 times×1.4 times) more floxed embryos were obtained relative to the case of the conventional method (one-step microinjection).

Further, as shown in FIG. 3, in either the microinjection or the electroporation, the two-step process showed production of more floxed individuals and a drastic decrease in chromosomal deletion among the offspring, compared to the one-step process. More specifically, while no floxed individual could be obtained by the conventional method (one-step microinjection), the two-step electroporation, which was most efficient, resulted in production of floxed individuals at 13%. In the case of the Tet3 gene, similarly to the case of the MeCP2 gene, the two-step electroporation successfully produced floxed individuals, and the efficiency was as high as 50% (4 individuals out of 8 individuals).

Figure 4:
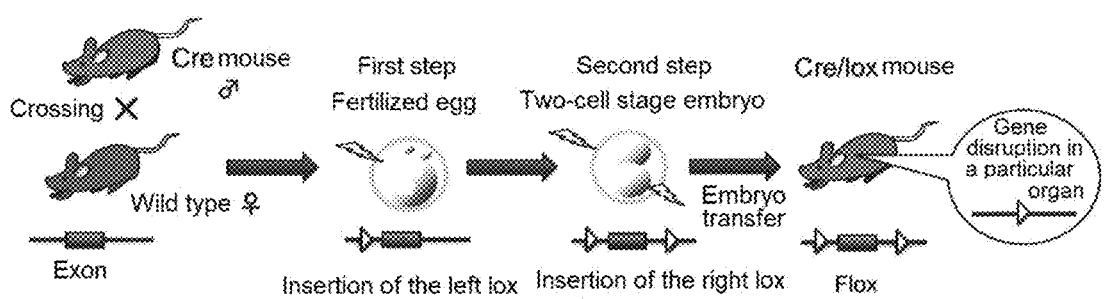
FIG. 4 is a diagram showing a procedure of construction of a floxed mouse using a fertilized egg that expresses Cre recombinase.

Separately, as shown in FIG. 4, two-step electroporation was applied by the same procedure to fertilized eggs that express Cre recombinase. As a result, floxed mice expressing Cre recombinase (Cre/lox mice) could be obtained with efficiencies of 20% (1 individual out of 5 individuals) in the case of the MeCP2 gene and 25% (1 individual out of 4 individuals) in the case of the Tet3 gene.

Thus, it was found that the two-step process, especially the two-step electroporation, enables efficient production of animals having a pair of recombinase recognition sequences on a chromosome, such as floxed mice. Further, it was found that, by application of the two-step method to fertilized eggs that express Cre recombinase, Cre/lox mice can be directly obtained.

INDUSTRIAL APPLICABILITY

According to the present invention, an animal having a pair of recombinase recognition sequences on a chromosome, such as a floxed animal, can be efficiently produced.

DESCRIPTION OF SEQUENCE LISTING

SEQ ID NOs:1 to 4: gRNA
SEQ ID NOs:5 to 8: ssODN
SEQ ID NO:9 to 12: Primers for genotype assay
SEQ ID NOs: 13 to 19: Wild-type recombinase recognition sequences
SEQ ID NOs:20 to 35: Variants of recombinase recognition sequences

What is claimed is:

1. A method of producing a transformed mouse, comprising:
   (A) introducing a first recombinase recognition sequence into a chromosome of a mouse cell;
   (B) introducing, after the Step (A), a second recombinase recognition sequence into the chromosome of the mouse cell; and
   (C) obtaining, after the Step (B), a transformed mouse having the first and second recombinase recognition sequences introduced into the chromosome,
   wherein the first and second recombinase recognition sequences are base sequences between which recombination occurs by a recombinase, and are introduced such that a target region on the chromosome is sandwiched between them,
   wherein the Step (A) is carried out in a fertilized egg, and the Step (B) is carried out in a two-cell stage embryo,
   wherein the introduction of the first and second recombinase recognition sequences is carried out by a CRISPR method comprising introducing into the mouse cell a Cas protein or a Cpf1 protein.

2. The method according to claim 1, wherein the first and second recombinase recognition sequences are loxP, VloxP, SloxP, rox, FRT, RS, or gix.

3. The method according to claim 1, wherein the recombinase is Cre, VCre, SCre, Dre, FLP, R, or Gin.

4. The method according to claim 1, wherein the CRISPR method comprises electroporation.

5. The method according to claim 1, wherein the CRISPR method comprises microinjection.

6. The method according to claim 1, wherein the target region is a region containing an exon of a target gene.

7. The method according to claim 1, wherein said method is a method of producing a conditional chromosome-modified mouse, wherein the mouse cell conditionally expresses the recombinase.

8. The method according to claim 7, wherein the conditional chromosome-modified mouse that conditionally expresses the recombinase is a mouse that tissue-specifically or period-specifically expresses the recombinase, or a mouse that expresses a recombinase that functions under drug-induced, tissue-specific, or period-specific conditions.

9. A method of producing a conditional chromosome-modified mouse, comprising:
- (A) introducing a first recombinase recognition sequence into a chromosome of a mouse cell;
- (B) introducing, after the Step (A), a second recombinase recognition sequence into the chromosome of the mouse cell; and
- (C) obtaining, after the Step (B), a transformed mouse having the first and second recombinase recognition sequences introduced into the chromosome, and
- (D) crossing the transformed mouse with a mouse that conditionally expresses a recombinase, to obtain a conditional chromosome-modified mouse,
- wherein the first and second recombinase recognition sequences are base sequences between which recombination occurs by the recombinase, and are introduced such that a target region on the chromosome is sandwiched between them,
- wherein the Step (A) is carried in a fertilized egg, and the Step (B) is carried out in a two-cell stage embryo,
- wherein the introduction of the first and second recombinase recognition sequences is carried out by a CRISPR method comprising introducing into the mouse cell a Cas protein or a Cpf1 protein.

10. The method according to claim 9, wherein the mouse that conditionally expresses the recombinase is a mouse that tissue-specifically or period-specifically expresses the recombinase, or a mouse that expresses a recombinase that functions under drug-induced, tissue-specific, or period-specific conditions.

* * * * *

```
                            SEQUENCE LISTING

<160> NUMBER OF SEQ ID NOS: 35

<210> SEQ ID NO 1
<211> LENGTH: 40
<212> TYPE: DNA
<213> ORGANISM: Artificial Sequence
<220> FEATURE:
<223> OTHER INFORMATION: gRNA

<400> SEQUENCE: 1
gcccaaggat acagtatcct agttttagag ctagaaatag                         40

<210> SEQ ID NO 2
<211> LENGTH: 40
<212> TYPE: DNA
<213> ORGANISM: Artificial Sequence
<220> FEATURE:
<223> OTHER INFORMATION: gRNA

<400> SEQUENCE: 2
caagttaaaa taaggctagt ccgttatcaa cttgaaaaag                         40

<210> SEQ ID NO 3
<211> LENGTH: 40
<212> TYPE: DNA
<213> ORGANISM: Artificial Sequence
<220> FEATURE:
<223> OTHER INFORMATION: gRNA

<400> SEQUENCE: 3
ggttcccagc aatggttctg ggttttagag ctagaaatag                         40

<210> SEQ ID NO 4
<211> LENGTH: 40
<212> TYPE: DNA
<213> ORGANISM: Artificial Sequence
<220> FEATURE:
<223> OTHER INFORMATION: gRNA

<400> SEQUENCE: 4
caagttaaaa taaggctagt ccgttatcaa cttgaaaaag                         40

<210> SEQ ID NO 5
<211> LENGTH: 40
<212> TYPE: DNA
```

```
<213> ORGANISM: Artificial Sequence
<220> FEATURE:
<223> OTHER INFORMATION: ssODN

<400> SEQUENCE: 5
ccagcaacct aaagctgtta agaaatcttt gggccccagc                               40

<210> SEQ ID NO 6
<211> LENGTH: 40
<212> TYPE: DNA
<213> ORGANISM: Artificial Sequence
<220> FEATURE:
<223> OTHER INFORMATION: ssODN

<400> SEQUENCE: 6
ttgacccaag gatacagtat gctagctacc gttcgtataa                               40

<210> SEQ ID NO 7
<211> LENGTH: 40
<212> TYPE: DNA
<213> ORGANISM: Artificial Sequence
<220> FEATURE:
<223> OTHER INFORMATION: ssODN

<400> SEQUENCE: 7
accaggggaa cgctgagacc ctggacgcac ttggcttcct                               40

<210> SEQ ID NO 8
<211> LENGTH: 40
<212> TYPE: DNA
<213> ORGANISM: Artificial Sequence
<220> FEATURE:
<223> OTHER INFORMATION: ssODN

<400> SEQUENCE: 8
gtcttcccag caatggttct ggatccataa cttcgtatag                               40

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
aagaagccaa ccatacagtg c                                                   21

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcttgctcag aagccaaaac                                                     20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
gaacgctgag accctggac                                                      19
```

```
<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
attcacacgt tggctctggt                                                    20

<210> SEQ ID NO 13
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 13
ataacttcgt atagcataca ttatacgaag ttat                                    34

<210> SEQ ID NO 14
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 14
tcaatttctg agaactgtca ttctcggaaa ttga                                    34

<210> SEQ ID NO 15
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 15
ctcgtgtccg ataactgtaa ttatcggaca tgat                                    34

<210> SEQ ID NO 16
<211> LENGTH: 32
<212> TYPE: DNA
<213> ORGANISM: Artificial Sequence
<220> FEATURE:
<223> OTHER INFORMATION: recombinase-recognition sequence

<400> SEQUENCE: 16
taactttaaa taatgccaat tatttaaagt ta                                      32

<210> SEQ ID NO 17
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 17
gaagttccta ttctctagaa agtataggaa cttc                                    34

<210> SEQ ID NO 18
<211> LENGTH: 31
<212> TYPE: DNA
<213> ORGANISM: Artificial Sequence
<220> FEATURE:
```

<223> OTHER INFORMATION: recombinase-recognition sequence

<400> SEQUENCE: 18
ttgatgaaag aatacgttat tctttcatca a                                31

<210> SEQ ID NO 19
<211> LENGTH: 26
<212> TYPE: DNA
<213> ORGANISM: Artificial Sequence
<220> FEATURE:
<223> OTHER INFORMATION: recombinase-recognition sequence

<400> SEQUENCE: 19
ttcctgtaaa ccgaggtttt ggataa                                      26

<210> SEQ ID NO 20
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 20
taccgttcgt ataatgtatg ctatacgaag ttat                             34

<210> SEQ ID NO 21
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 21
taccgttcgt atagcataca ttatacgaag ttat                             34

<210> SEQ ID NO 22
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 22
ataacttcgt atagtataca ttatacgaag ttat                             34

<210> SEQ ID NO 23
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 23
ataacttcgt ataggatact ttatacgaag ttat                             34

<210> SEQ ID NO 24
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 24
ataacttcgt ataccttt ctatacgaag ttat                               34

<210> SEQ ID NO 25
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 25
ataacttcgt atagcataca ttatacgaac ggta                                34

<210> SEQ ID NO 26
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 26
taccgttcgt atagcataca ttatacgaag ttat                                34

<210> SEQ ID NO 27
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 27
tcaatttctg agaagtgtct ttctcggaaa ttga                                34

<210> SEQ ID NO 28
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 28
tcaatttccg agaactgtca ttctcggaaa ttga                                34

<210> SEQ ID NO 29
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 29
tcaatttctg agaactgtca ttctcagaaa ttga                                34

<210> SEQ ID NO 30
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 30
tcaatttctg agaactgtca ttctcggaat acct                                34

<210> SEQ ID NO 31
<211> LENGTH: 34
<212> TYPE: DNA
<213> ORGANISM: Artificial Sequence
<220> FEATURE:
<223> OTHER INFORMATION: recombinase-recognition sequence

```
<400> SEQUENCE: 31
cgtgattctg agaactgtca ttctcggaaa ttga                                34

<210> SEQ ID NO 32
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 32
ctcgtgtccg ataagtgtat ttatcggaca tgat                                34

<210> SEQ ID NO 33
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 33
ctcgtgtccg ataactgtaa ttatcggaca cgag                                34

<210> SEQ ID NO 34
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 34
ctcgtgtccg ataactgtaa ttatcggacc gtca                                34

<210> SEQ ID NO 35
<211> LENGTH: 34
<212> TYPE: DNA
<213> ORGANISM: Artificial Sequence
<220> FEATURE:
<223> OTHER INFORMATION: recombinase-recognition sequence

<400> SEQUENCE: 35
tgacggtccg ataactgtaa ttatcggaca tgat                                34
```